United States Patent
Rappaport et al.

(10) Patent No.: US 6,450,956 B1
(45) Date of Patent: Sep. 17, 2002

(54) SYSTEM AND METHOD FOR TREATMENT AND OUTCOME MEASUREMENT ANALYSIS

(75) Inventors: David R. Rappaport, Marlboro; Nugroho Iwan Santoso, Plainsboro, both of NJ (US)

(73) Assignee: Siemens Corporate Research, Inc., Princeton, NJ (US)

(*) Notice: Subject to any disclaimer, the term of this patent is extended or adjusted under 35 U.S.C. 154(b) by 13 days.

(21) Appl. No.: 09/706,631

(22) Filed: Nov. 6, 2000

(51) Int. Cl.[7] .................................................. A61B 5/00
(52) U.S. Cl. ........................................................ 600/300
(58) Field of Search .................................. 600/300, 301; 128/897–925

(56) References Cited

U.S. PATENT DOCUMENTS

| | | | | |
|---|---|---|---|---|
| 5,018,067 A | * | 5/1991 | Mohlenbrock et al. | 600/300 |
| 5,738,102 A | * | 4/1998 | Lemelson | 128/903 |
| 5,769,074 A | * | 6/1998 | Barnhill et al. | 600/300 |
| 5,860,917 A | * | 1/1999 | Comanor et al. | 600/300 |
| 6,063,028 A | * | 5/2000 | Luciano | 600/300 |

* cited by examiner

Primary Examiner—Kevin Shaver
Assistant Examiner—David McCrosky
(74) Attorney, Agent, or Firm—Donald B. Paschburg

(57) ABSTRACT

A system and method for providing treatment and outcome measurement analysis. In one aspect, real-time treatment options having statistical outcome data are generated and provided to users. Data from remote data sources is compiled onto a server and used to generate a decision support model. The user can then present patient features to the decision support model, and will be provided with a set of possible treatment options with statistical information in return. When a user selects a treatment option, an outcome analysis is performed to assess the patient's progress. The results of the outcome analysis are input into the server to update the decision support model.

23 Claims, 1 Drawing Sheet

SYSTEM AND METHOD FOR TREATMENT AND OUTCOME MEASUREMENT ANALYSIS

BACKGROUND

1. Technical Field

The present invention relates generally to a decision support system, and in particular, a closed loop medical decision support system for generating real-time treatment options having statistical outcome data.

2. Description of Related Art

A great number of people depend on and receive healthcare services from clinicians. Clinicians base their treatment plans mainly on retrospective analysis and successful past experiences. For example, a particular doctor may have his own opinion of a preferred drug for use on a specific condition based on his observation of how the drug had performed on his past patients with the same condition. Such a decision-making process for treatment is therefore based on a relatively small pool of information which focuses on a single doctor's personal preferences and therefore lacks any real significance or validity. Similarly, when hospitals and clinics base their treatment choices on past successful experiences, although each hospital or clinic may provide a somewhat larger database of past information, such information is still localized and skewed for that particular location.

Making a medical decision as to treatment based on only an individual's or a hospital's past successful experiences can be risky. An ill-advised or inappropriate decision leads to uncured and potentially more seriously ill patients, more disabilities and complications, higher costs of care, and lower confidence in the health care industry. However, physicians often lack the time to conduct detailed research on treatment options for every condition, especially for complicated conditions and when an emergency arises demanding immediate attention.

Accordingly, an efficient and accurate system for providing a clinician or physician with real-time detailed information on treatment options and respective outcome measurements at the point of care for a particular condition, is highly desirable.

SUMMARY OF THE INVENTION

The present invention is directed to a method of providing the optimal current treatment suggestions for a particular condition. In one aspect of the present invention, a method of generating and providing treatment options and outcome analyses over a communication network is provided comprising the steps of: filtering data from a plurality of remote databases and a local database; compiling said data in a server; providing the server with a plurality of conditions; constructing a plurality of decision support models using the data, wherein each decision support model generates output comprising a plurality of real-time treatment options including statistical information for treating each of the plurality of conditions; providing patient features to the decision support model; matching said patient features to a corresponding condition of said plurality of conditions; presenting a subscriber with said plurality of real-time treatment options for treating the patient features, wherein upon selection by the subscriber of one of said plurality of real-time treatment options, the server further includes the steps of performing an outcome analysis for assessing a result of said selected treatment option, and automatically updating the statistical information of the treatment option using the result.

In another aspect of the present invention, a method of generating and providing treatment options and outcome analyses over a communication network is provided comprising the steps of filtering data from a plurality of remote databases and a local database; compiling said data in a server; providing the server with a plurality of conditions; constructing a decision support model using the data, wherein the decision support model generates output comprising a plurality of real-time treatment options including statistical information for treating each of the plurality of conditions; providing patient features to the decision support model; matching said patient features to a corresponding condition of said plurality of conditions; presenting a subscriber with said plurality of real-time treatment options for treating the patient features, wherein upon selection by the subscriber of one of said plurality of real-time treatment options, the server further includes the steps of performing an outcome analysis for assessing a result of said selected treatment option; and automatically updating the statistical information of the treatment option using the result.

These and other aspects, features, and advantages of the present invention will become apparent from the following detailed description of the preferred embodiments, which is to be read in connection with the accompanying drawing.

DETAILED DESCRIPTION OF PREFERRED EMBODIMENTS

Figure 1:
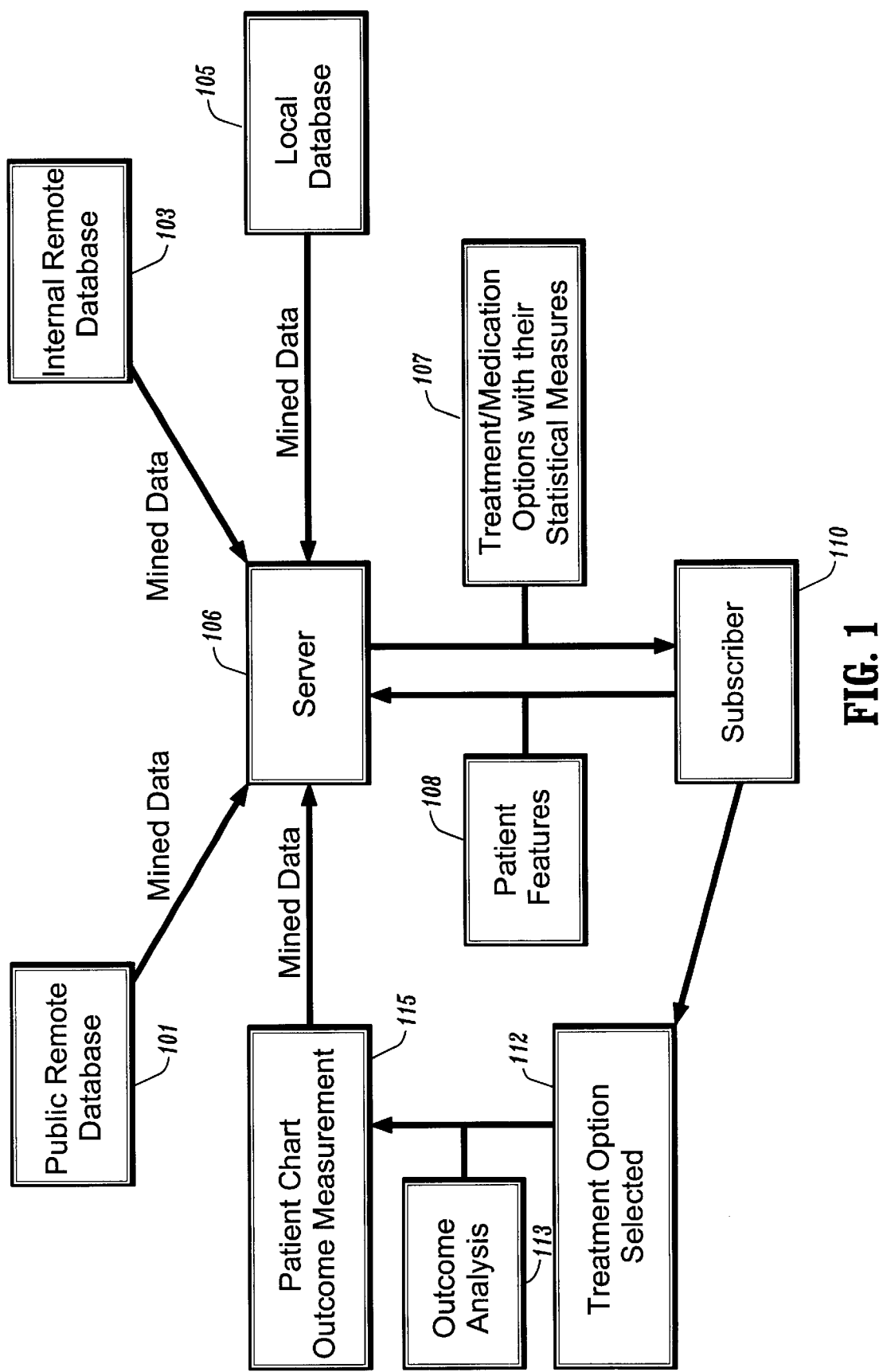
FIG. 1 depicts an exemplary flow diagram of a decision support system for enabling a treatment and outcome measurement analysis according to one aspect of the present invention.

It is to be understood that the exemplary system modules and method steps described herein may be implemented in various forms of hardware, software, firmware, special purpose processors, or a combination thereof. Preferably, the present invention is implemented in software as an application program tangibly embodied on one or more program storage devices. The application program may be executed by any machine, device or platform comprising suitable architecture. It is to be further understood that, because some of the constituent system modules and method steps depicted in the accompanying Figures are preferably implemented in software, the actual connections between the system components (or the process steps) may differ depending upon the manner in which the present invention is programmed. Given the teachings herein, one of ordinary skill in the related art will be able to contemplate or practice these and similar implementations or configurations of the present invention.

FIG. 1 depicts an example of a flow diagram of a decision support system for enabling a treatment and outcome measurement analysis according to one aspect of the present invention. The decision support system can be divided into 3 stages. Initially in stage 1, a database is developed in which relevant clinical information is filtered or mined over a communication network, for example, the Internet, from various data sources such as a public remote database 101, an internal remote database 103 and a local database 105. Public database 101 can include online sources of free clinical data for use by the general public, such as, for example, the U.S. Department of Health and Human Services. Internal database 103 can be, for example, a private internal database belonging to particular hospital, or a SMS (Shared Medical System) for providing clinical data. Local database 105 can comprise, for example, clinical data such as temperature and laboratory information, EKG results, etc., of patients in a hospital from an internal hospital monitoring system.

The clinical data can be filtered and classified according to specific cases or medical conditions or a group of diagnoses and conditions, following, for example, the standard international code of diagnoses (ICD-9 coding system). A condition may include, for example, a physical state of a patient or a disease that the patient is suffering from.

The mined data from the various data sources is then compiled in a database on a server 106 and used to generate a decision support model. A decision support model comprises a compressed statistical representation of the data and can be, for example, modular (individually constructed for each particular condition), or generated as one large model covering all specified conditions. For each condition, the decision support model generates statistically significant probabilities of various feasible treatments.

The decision support model can be constructed, for example, by using probability reasoning techniques (see "Nuclear Plant Fault Diagnosis Using Probabilistic Reasoning", Proc. of the 1999 IEEE Power Engineering Society Summer Meeting) which provide a way to capture knowledge and reach rational decisions in uncertain domains, and support a mathematical explanation of the results, which is necessary in many critical applications.

Various data filtering and classification techniques can be used for generating the data required for building the decision support model. For example, the filtering process can be done off-line according to pre-determined case classifications or conditions, in which conditions are specified and all information relevant to each condition is then filtered or "mined" from the databases to build the decision support model. The filtering process can also be done on-line, which typically happens when a particular patient has a condition which has not been filtered for before. That patient's data can be input to the server 106 to filter new relevant information from the public database 101, internal remote database 103 and local database 105 to build a new decision support model (if, for example, the decision support model is modular), or update an existing decision support model (if, for example, there is a single decision support model covering all specified conditions).

In stage 2 of the system of the present invention, a triggering event such as, for example, a diagnosis being made, changes in a patient's condition, an alarm from the hospital monitoring system going off due to an emergency, or a clinician and/or physician inputting a patient's data, can initiate the process of generating statistically significant probabilities of various feasible treatments for that specific condition. For example, once the decision support model is generated or "trained", information on a particular patient's condition or patient features (e.g., patient symptoms, test results, previous treatments, diagnosis) extracted from the patient's data can then be presented to the decision support model by a subscriber 110 (step 108). The subscriber 110 can include, for example, a clinician, a physician, or a hospital monitoring system. The decision support model will provide a set of possible treatment and medication options which includes statistical information on each suggested treatment or medication option (step 107). This statistical information can be based on the statistical success in the past of available similar cases (diagnoses and treatment outcomes) stored in the database of server 106.

To illustrate, the decision support model can suggest 3 different antibiotics A, B and C for treating a particular condition, for example, a staph infection, and indicate that 72% of patients with a staph infection responded well to antibiotic A, 67% responded well to antibiotic B, and 62% to antibiotic C. Such statistical information can also be ranked and a top 5, 10, etc., list of medications can be created. In addition, the decision support model can compile other statistical information computed from the remote and local databases, including, for example, the percentage of patients who experienced certain side effects from each suggested treatment, and discrepancies in success/side effect rates among patients of varying ages, blood pressure levels, weight, etc.

The treatment and medication options including the statistical information are provided to the subscriber 110 of the system, preferably at the point of care. The point of care is where treatment is actually implemented. Advantageously, the dynamic and real-time characteristics of Internet usage are captured in this feature. The treatment and statistical information can be transmitted to, for example, a wireless device such as a Palm Pilot, a patient monitoring computer, or to a desktop computer terminal. This enables a clinician or a physician either in his/her office or in the field to instantaneously be notified of and presented with, for example, a patient's diagnosis and a list of real-time potential treatment options with statistical information on each treatment's success rate, occurrence of side effects, etc.

A treatment option is then selected by the subscriber 110 (step 112) using the information provided in step 107. This triggers stage 3 of the system of the present invention, in which an outcome analysis 113 is performed. In an outcome analysis, a patient's progress from the point when he started the selected medication or treatment to his time of discharge is analyzed. The results of the outcome analysis 113 are recorded on the patient's chart (step 115) and then input into the server 106 to form a closed feedback loop. If the patient's outcome analysis resulted in a successful treatment from using antibiotic A, for example, the "old" statistical success rate of antibiotic A for that patient's particular condition will be updated to reflect the success in this instance, thus resulting in a new increased success rate for antibiotic A when used for that particular patient's condition.

In an alternative embodiment, if the communication bandwidth between the subscriber 110 and the server 106 becomes restrictive (i.e., if the server is "down"), the decision support model can be duplicated and reside in a mirror server at the subscriber's computer. Updates and communications between the server 106 and the mirror server can be done off-line at predetermined times. On-line requests from the subscriber can be handled locally by the mirror server. This alternative provides increased reliability for subscribers, since the on-line processes do not depend on outside networks.

Advantageously, the closed feedback loop feature provides for an automatic and continuous updating system in which the decision support system is constantly being "trained" with new information in a continuous learning process. This enables physicians to be informed of the best current treatment options available based on a massive pool of database information. In addition, it also becomes readily apparent when, for example, certain drugs begin to lose their effectiveness, i.e., when certain bacteria strains become resistant to some antibiotics.

Overall, the present invention would enable clinicians and/or physicians to make better-informed decisions for complicated medical conditions which would increase the quality of healthcare provided. The ability of a clinician or physician to have real-time statistical data on outcomes of specific treatment options will greatly increase the quality, efficiency, and productivity of the healthcare delivered.

In addition, hospitals can enhance their competitive edge by reducing hospital stays in an inpatient care setting. Average hospital stays for various conditions will be decreased since patients will be properly treated by a statistically proven treatment in a faster time.

It is to be appreciated that a method according to the present invention is not limited to the domain of health care and can be applied to other fields. For example, the process of the present invention can be utilized in financial areas such as stock analysis by including a decision support system for generating real-time performance ratings, benchmarking tools, etc., for access by, for example, a stockbroker at the point of sale.

Although illustrative embodiments of the present invention have been described herein with reference to the accompanying drawing, it is to be understood that the present invention is not limited to those precise embodiments, and that various other changes and modifications maybe affected therein by persons ordinarily skilled in the art without departing from the scope or spirit of the invention. All such changes and modifications are intended to be included within the scope of the invention as defined by the appended claims.

What is claimed is:

1. A method of generating and providing treatment options and outcome analyses over a communication network comprising the steps of:
    filtering data from a plurality of remote databases and a local database;
    compiling said data in a server;
    providing the server with a plurality of physical conditions;
    constructing a plurality of decision support models using the data, wherein each decision support model generates output comprising a plurality of real-time treatment options including statistical success information of each option for treating each of the plurality of physical conditions;
    providing patient features to the decision support model;
    matching said patient features to a corresponding physical condition of said plurality of physical conditions;
    presenting a subscriber with said plurality of real-time treatment options including statistical success information of each option for treating the patient features, wherein upon selection by the subscriber of one of said plurality of real-time treatment options, the server further includes the steps of:
        performing an outcome analysis for assessing a result of said selected treatment option; and
        automatically updating the statistical success information of the treatment option using the result.

2. The method of claim 1, wherein the data comprises clinical data.

3. The method of claim 1, wherein the remote databases include a public remote database and an internal remote database.

4. The method of claim 1, wherein the local database comprises clinical data of a plurality of patients in a hospital.

5. The method of claim 1, wherein the plurality of physical conditions include physical states and diseases.

6. The method of claim 1, wherein the plurality of physical conditions comprise a group of diagnoses and physical conditions according to an ICD-9 coding system.

7. The method of claim 1, wherein the patient features includes one or more of a patient's test results, changes in the patient's physical condition, an emergency, symptoms, previous treatments and symptoms, and a diagnosis.

8. The method of claim 1, wherein the patient features are provided to the decision support model by a hospital monitoring system.

9. The method of claim 1, wherein if the patient features are not matched to a corresponding physical condition, further comprising the steps of:
    providing the server with the patient features;
    automatically constructing a new decision support model using the data, wherein the new decision support model generates output comprising a plurality of real-time treatment options including statistical success information for treating the patient features;
    presenting a subscriber with said plurality of real-time treatment options including statistical success information of each option for treating the patient features, wherein upon selection by the subscriber of one of said plurality of real-time treatment options, the server further includes the steps of:
        performing an outcome analysis for assessing a result of said selected treatment option; and
        automatically updating the statistical success information of the treatment option using the result.

10. The method of claim 1, wherein the subscriber is presented with said plurality of treatment options by one or more of computers, remote communication devices, and wireless devices.

11. The method of claim 1, wherein the subscriber is a clinician.

12. The method of claim 1, wherein the subscriber is a hospital monitoring system.

13. A method of generating and providing treatment options and outcome analyses over a communication network comprising the steps of:
    filtering data from a plurality of remote databases and a local database;
    compiling said data in a server;
    providing the server with a plurality of physical conditions;
    constructing a decision support model using the data, wherein the decision support model generates output comprising a plurality of real-time treatment options including statistical success information of each option for treating each of the plurality of physical conditions;
    providing patient features to the decision support model;
    matching said patient features to a corresponding physical condition of said plurality of physical conditions;
    presenting a subscriber with said plurality of real-time treatment options including statistical success information of each option for treating the patient features, wherein upon selection by the subscriber of one of said plurality of real-time treatment options, the server further includes the steps of:
        performing an outcome analysis for assessing a result of said selected treatment option; and
        automatically updating the statistical success information of the treatment option using the result.

14. The method of claim 13, wherein the data comprises clinical data.

15. The method of claim 13, wherein the remote databases include a public remote database and an internal remote database.

16. The method of claim 13, wherein the local database comprises clinical data of a plurality of patients in a hospital.

17. The method of claim 13, wherein the plurality of physical conditions include physical states and diseases.

18. The method of claim 13, wherein the plurality of physical conditions comprise a group of diagnoses and physical conditions according to an ICD-9 coding system.

19. The method of claim 13, wherein the patient features are provided to the decision support model by a hospital monitoring system.

20. The method of claim 13, wherein if the patient features are not matched to a corresponding physical condition, further comprising the steps of:

provevaluating the server with the patient features;

automatically updating the decision support model using the data to produce an updated decision support model, wherein the updated decision support model generates output comprising a plurality of real-time treatment options including statistical success information for treating the patient features;

presenting a subscriber with said plurality of real-time treatment options including statistical success information of each option for treating the patient features, wherein upon selection by the subscriber of one of said plurality of real-time treatment options, the server further includes the steps of:

performing an outcome analysis for assessing a result of said selected treatment option; and automatically updating the statistical success information of the treatment option using the result.

21. The method of claim 13, wherein the subscriber is presented with said plurality of treatment options by one or more of computers, remote communication devices, and wireless devices.

22. The method of claim 13, wherein the subscriber is a physician.

23. A program storage device readable by machine, tangibly embodying a program of instructions executable by the machine to perform the method steps for generating and providing treatment options and outcome analysis over a communication network, the method comprising the steps of:

filtering data from a plurality of remote databases and a local database;

compiling said data in a server;

providing the server with a plurality of physical conditions;

constructing a plurality of decision support models using the data, wherein each decision support model generates output comprising a plurality of real-time treatment options including statistical success information of each option for treating each of the plurality of physical conditions;

providing patient features to the decision support model;

matching said patient features to a corresponding physical condition of said plurality of physical conditions;

presenting a subscriber with said plurality of real-time treatment options including statistical success information of each option for treating the patient features, wherein upon selection by the subscriber of one of said plurality of real-time treatment options, the server further includes the step of:

performing an outcome analysis for assessing a result of said selected treatment option; and automatically updating the statistical success information of the treatment option using the result.

* * * * *